United States Patent
Klopping

[11] 3,979,518
[45] Sept. 7, 1976

[54] FUNGICIDAL ALKOXY SUBSTITUTED 2-CYANOACETAMIDE DERIVATIVES

[75] Inventor: Hein Louis Klopping, Wilmington, Del.

[73] Assignee: E. I. Du Pont de Nemours and Company, Wilmington, Del.

[22] Filed: Sept. 11, 1975

[21] Appl. No.: 612,547

[52] U.S. Cl. .............................. 424/304; 260/465.4
[51] Int. Cl.² ................. A01N 9/20; C07C 121/417
[58] Field of Search .................. 260/465.4; 424/304

[56] References Cited
UNITED STATES PATENTS

| | | |
|---|---|---|
| 2,313,498 | 3/1943 | Allen et al. .................. 260/465.4 X |
| 3,496,214 | 2/1970 | Meindl et al. .................. 260/465.4 |
| 3,625,987 | 12/1971 | Hubele ............................ 424/304 X |
| 3,803,320 | 4/1974 | Brechbuhler et al. ............. 424/304 |

FOREIGN PATENTS OR APPLICATIONS

| | | |
|---|---|---|
| 2,436,654 | 2/1975 | Germany |
| 2,436,655 | 2/1975 | Germany |
| 2,350,910 | 4/1974 | Germany |

*Primary Examiner*—Joseph Paul Brust

[57] ABSTRACT

Compounds of the formula

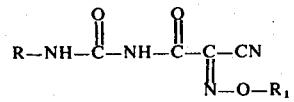

where
R is $CH_3OCH_2-$ or $CH_3O(CH_2)_3-$ and $R_1$ is alkyl of 1 or 2 carbon atoms are effective plant disease control agents.

5 Claims, No Drawings

FUNGICIDAL ALKOXY SUBSTITUTED 2-CYANOACETAMIDE DERIVATIVES

BACKGROUND OF THE INVENTION

This invention relates to fungicidal compounds and their use in controlling plant diseases.

There are many commercial formulations available for control of fungus diseases of plants. However, new fungicides are needed to provide better control of particular plant diseases, and control strains of fungi which are not susceptible to commercially available products. The compounds of this invention are particularly effective against certain Phycomycetes, for example, late blight of tomato and potato and downy mildew of grapes. Unlike many commercially available products the compounds of this invention not only prevent the attack of a fungus against plants, they also can eradicate the fungus after the plant has become infected.

SUMMARY OF THE INVENTION

Compounds of the formula

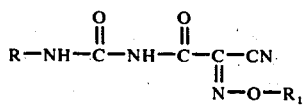

wherein R is $CH_3OCH_2-$ or $CH_3O(CH_2)_3-$ and $R_1$ is alkyl of 1 or 2 carbon atoms are useful in inhibiting fungus diseases in plants. Disease control includes the prevention, inhibition and/or eradication of a plant disease.

The compounds of this invention may be applied to plants to prevent infection of the plants by fungi. The compounds are not only preventive in their action but are also systemic and curative. That is, the compounds are absorbed by plants and move within the plants. Thus they can eradicate a fungus which has already infected the plant. Because the compounds are systemic they may be applied not only to the infected or threatened plant parts but also to uninfected parts or to the soil in which the plant grows. All of these sites of application are included within the term "applying to the plants".

The fact that the compounds of this invention are systemic makes them particularly well suited for combination with conventional preventive fungicides. Thus, the compositions of this invention consist essentially of a fungicidally effective amount of a compound of this invention but another fungicidally active ingredient and conventional formulating agents can also be included.

The compounds of this invention wherein $R_1$ is methyl, 2-cyano-2-methoxyimino-N-methoxymethylcarbamoylacetamide and 2-cyano-2-methoxyimino-N-(3'-methoxypropyl)carbamoylacetamide are preferred for their fungicidal activity.

DETAILED DESCRIPTION OF THE INVENTION

The compounds of this invention can be prepared by two different routes.

In the first of these routes, 2-cyano-2-methoxyiminoacetamide (O. Diels and E. Borgwardt, Ber. 54, 1342 (1921)) or a corresponding higher alkoxyimino homolog of this starting material is converted to the anion of the amide, for example by means of sodium methoxide or sodium hydride in a suitable inert solvent such as tetrahydrofuran. This anion is reacted with an isocyanate R—NCO, where R is $CH_3OCH_2-$ or $CH_3O(CH_2)_3-$. This reaction affords the anion of the product; the product is obtained by acidification in aqueous medium.

In the second of these two routes, an amine $R-NH_2$ is converted to the corresponding urea by means of a cyanate such as potassium cyanate, and the urea is reacted with cyanoacetic acid and acetic anhydride to give a cyanoacetyl urea of the general formula

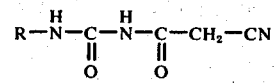

This intermediate is then converted to the oxime by means of sodium nitrite or a suitable alkyl nitrite by methods known in the art. The hydroxy-imino group is alkylated by known methods, for example by conversion to the sodium salt by means of sodium methoxide using DMF as the solvent, and adding the appropriate alkylating agent. Suitable alkylating agents include alkyl iodides and bromides. Dialkyl sulfates may also be used.

The compounds of this invention are useful as plant disease control agents. They have qualities of systemic and curative activity when applied to soil, to propagation pieces, to stems, or to foliage. Combinations with other fungicides, especially those with strong residual properties, provide particularly exceptional disease control. The systemic and curative effects of the disease-control agents of this invention make a unique contribution to such combinations. For this reason, compositions containing another fungicide along with a compound of this case are often preferred. The systemic property of the compounds of this case is strikingly evident in the control of potato and tomato late blight disease on the foliage when treatments with the compounds are applied solely to the root system. Additional evidence comes from the curative action against established infections by the causal agent of late blight disease or downy mildew of grapes. The diseases can be arrested even when treatments are delayed hours after plants have been infected.

Of the fungi causing diseases on agricultural crops, those classed as Phycomycetes are among the most virulent. The disorders caused by this group of fungi include late blight of tomatoes and potatoes, as well as downy mildew of grapes, cole crops, legumes, and cucurbits. Diseases caused by Phycomycetes are especially susceptible to control by the compounds of this invention.

The compounds of this invention provide protection from damage caused by certain fungi when applied to the plants by the methods described hereinafter and at a sufficient rate to exert the desired effect. They are suited for the protection of living plants by applying the compounds of this invention to the soil in which they are growing or in which they may subsequently be seeded or planted, to seeds, tubers, bulbs, or other plant reproductive parts prior to planting, as well as to foliage, stems, and/or fruit. Soil applications are made from dusts, granules, pellets, solutions, emulsions, or slurries.

Preferred rates for application of the compounds of this invention to soil in which plants are or will be growing range from 0.5 to 500 ppm by weight of the soil in which the roots are or will be growing. More preferred use rates are in the range of 1 to 200 parts per million. The most preferred rates are in the range of 5 to 100 ppm. Preferred rates for application to seeds, tubers, bulbs, or other plant reproductive parts range from 0.5 to 100 g of active compound of this invention per kilo of planting material treated. More preferred rates are in the range of 1 to 75 g of active compound per kilo. The most preferred rates are in the range of 2 to 50 g per kilo. Applications of this type are made from dusts, slurries, emulsions, or solutions.

Preferred rates of application for the compounds of this invention to foliage, stems, and/or fruit of living plants range from 0.05 to 20 kilograms of active ingredient per hectare. More preferred rates are in the range of 0.1 to 10 kilos per hectare. The most preferred rates are in the range of 0.2 to 5 kilograms per hectare. The optimum amount within this range depends upon a number of variables which are well known to those skilled in the art of plant protection. The variables include, but are not limited to, the disease to be controlled, weather conditions expected, the type of crop, stage of development of the crop, and the interval between applications. Applications within the range given may need to be repeated one or many more times at intervals of 1 to 60 days. Applications are made from dusts, slurries, emulsions, or solutions.

The compositions of the invention can contain, in addition to the active ingredient of this invention, conventional insecticides, miticides, bactericides, nematicides, fungicides, or other agricultural chemicals such as fruit set agents, fruit thinning compounds, fertilizer ingredients and the like. Combinations with other fungicides, particularly maneb, captafol and chlorthalonil, are often preferred. The additional agricultural chemicals are employed in mixtures or combinations in amounts ranging from one to twenty times that of the compound or compounds of this invention. The proper choice of the additive chemical and amounts is readily made by one skilled in the art of protecting plants from pest depredations. The following are illustrative of the agricultural chemicals that may be included in compositions of the compounds of this invention or, additionally, that may be added to sprays containing one or more of the active compounds of this invention:

bis(dimethylthiocarbamoyl)disulfide or tetramethylthiuram disulfide (thiram);
metal salts of ethylenebisdithiocarbamic acid or propylenebisdithiocarbamic acids, e.g. manganese, zinc, iron and sodium salts (maneb or zineb);
n-dodecylguanidine acetate (dodine);
N-(trichloromethylthio)phthalimide (folpet);
N-[(trichloromethyl)thio]-4-cyclohexene-1,2-dicarboximide (captan);
cis-N-[(1,1,2,2-tetrachloroethyl)thio]-4-cyclohexene-1,2-dicarboximide (captafol);
2,4-dichloro-6-(o-chloroanilino)-s-triazine ("Dyrene");
3,3'-ethylenebis(tetrahydro-4,6-dimethyl-2H-1,3,5-thiadiazine-2-thione), (milneb);
triphenyltin hydroxide (fentin hydroxide);
triphenyltin acetate (fentin acetate);
N'-dichlorofluoromethylthio-N,N-dimethyl-N'-phenylsulfamide (dichlorfluanid);
tetrachloroisophthalonitrile (chlorthalonil);
tribasic copper sulfate;
fixed copper;
sulfur;
methyl 1-(butylcarbamoyl)-2-benzimidazolecarbamate (benomyl);
methyl 2-benzimidazolecarbamate;
1,2-bis(3-methoxycarbonyl-2-thioureido)benzene (methyl thiophanate).

The agricultural chemicals listed above are merely exemplary of the compounds which can be mixed with the active compounds of this invention and are not intended to any way limit the invention.

The use of pesticides in combination with a compound within the scope of this invention sometimes appears to greatly enhance the activity of the active compound of the invention. An unexpected degree of activity is sometimes seen when another pesticide is used along with the methods of this invention.

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 1% to 99% by weight of active ingredient(s) and at least one of a) about 0.1% to 20% surfactant(s) and b) about 5% to 99% solid or liquid diluent(s). More specifically, they will contain these ingredients in the following approximate proportions:

|  | Active Ingredient | Percent by Weight | |
|---|---|---|---|
|  |  | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, or course, be present depending on the intended use and the physical properties of the compound. Higher ratios of surfactant to active ingredient are sometimes desirable, and are achieved by incorporation into the formulation or by tank mixing. Likewise, oils or humectants may be incorporated or tank mixed.

Typical solid diluents are described in Watkins et al., "Handbook of Insecticide Dust Diluents and Carriers", 2nd Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0°C. "McCutcheon's Detergents and Emulsifiers Annual", Allured Publ. Corp., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, control pH, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. e. Browning, "Agglomeration", *Chemical Engineering*, Dec. 4, 1967, pp. 147ff. and "Perry's Chemical Engineer's Handbook", 4th. Edn., McGrawHill, N.Y., 1963, pp. 8–59ff.

For further information regarding the art of formulation, see for example:

- J. B. Buchanan, U.S. pat. No. 3,576,834, Apr. 27, 1971, Col. 5 Line 36 through Col. 7 Line 70 and Ex. 1–4, 17, 106, 123-140.
- R. R. Shaffer, U.S. Pat. No. 3,560,616, Feb. 2, 1971, Col. 3 Line 48 through Col. 7 Line 26 and Examples 3–9, 11–18.
- E. Somers, "Formulation", Chapter 6 in Torgeson, "Fungicides", Vol. I, Academic Press, New York, 1967.

The following examples further illustrate the invention. All parts and percentages are by weight.

EXAMPLE 1

Preparation of 2-Cyano-2-methoxyimino-N-(methoxymethylcarbamoyl)acetamide

To a suspension of 2.70 g. of 2-cyano-2-methoxyiminoacetamide in 10 ml. of tetrahydrofuran was added 1.20 g. of a 55% suspension of sodium hydride in mineral oil in portions with stirring. After stirring for 15 minutes, 2.40 g. of methoxymethylisocyanate was added dropwise. The mixture was stirred at 50°C. for 3 minutes to ensure completion of the reaction. The mixture was then cooled in an ice bath, and a solution of 1.9 ml. of acetic acid in 120 ml. of ice water was added rapidly with stirring. After stirring for another 25 minutes, 2-cyano-2-methoxyimino-N-methoxymethyl-carbamoylacetamide was collected on a filter, washed with water and ether, and dried. The product weighed 2.7 g. and melted at 163.5°–165°C.

EXAMPLE 2

Preparation of 2-Cyano-2-methoxyimino-N-(3'-methoxypropyl)-carbamoylacetamide 3-Methoxypropyl urea was prepared from methoxypropylamine and potassium cyanate. Seventy-six grams of this product was mixed with 43 g. of cyanoacetic acid and 100 ml. of acetic anhydride. The mixture was stirred and heated on a steam bath. When the temperature of the mixture reached 85°C., heat of reaction evolved and external cooling was applied to keep the temperature under control. After stirring for 1 hour on the steam bath, the mixture was cooled. The cyanoacetyl urea was recovered by filtration, washing with ether and drying. Yield 77.5 g., mp 128.5–130.5°.

Seventy grams of the above urea was suspended in 560 ml. of acetic acid. The suspension was cooled to 5–10°C., and a solution of 42 g. of sodium nitrite in 65 ml. of $H_2O$ was slowly added with stirring. After stirring overnight, 35 ml. of hydrochloric acid was slowly added, and the solution was vacuum concentrated to dryness. The residue was triturated with about an equal volume of water and cooled in ice. 2-Cyano-2-hydroxyimino-N-(3'-methoxypropyl)carbamoylacetamide was obtained by filtering, washing with ice water, and drying, and was pure enough for use in the next step.

The hydroxyimino compound, 4.5 g., was dissolved in 25 ml. of acetone, and 1.6 g. of powdered anhydrous potassium carbonate and 2.2 ml. of dimethyl sulfate were added. The mixture was heated to reflux and stirred for 2 hours. It was then cooled in ice and treated with ice water. The product precipitated. It was filtered, washed with water and ether, and dried. yield 4 g., mp 126°–127°.

EXAMPLE 3

2-Ethoxyimino-2-cyanoacetamide can be prepared by the reaction of 2-cyano-2-hydroxyiminoacetamide with an alkylating agent in the presence of a base such as potassium carbonate in an inert solvent such as DMF. By reacting the 2-ethoxyimino-2-cyanoacetamide with methoxymethyl isocyanate by the method of Example 1, 2-cyano-2-ethoxyimino-N-methoxymethyl-carbamoylacetamide, mp 124°–125°C. can be made.

EXAMPLE 4

According to the method of Example 2, reacting 2-cyano-2-hydroxyimino-N-(3'-methoxypropyl)carbamoylacetamide with ethyl bromide, 2-cyano-2-ethoxyimino-N-(3'-methoxypropyl)carbamoylacetamide can be prepared.

EXAMPLE 5

A wettable powder formulation can be made and applied as follows:

|  | Percent |
|---|---|
| 2-cyano-2-methoxyimino-N-methoxymethyl-carbamoylacetamide | 50 |
| sodium alkylnaphthalenesulfonate | 2 |
| low-viscosity methylcellulose | 2 |
| diatomaceous earth | 46 |

The ingredients are blended, coarsely hammer-milled and then air-milled to produce particles of active compound essentially all below 20 microns in diameter. The product is reblended before packaging.

All compounds of the invention may be formulated similarly.

This formulation is dispersed in water in an amount sufficient to provide a concentration of 400 ppm of the active compound of this invention. The dispersion is sprayed to the point of run-off on potted tomato plants and allowed to dry. Both treated and untreated plants are inoculated with a spore suspension of *Phytophthora infestans* and incubated for a day in a saturated humidity chamber, After five days of additional incubation in the greenhouse, all of the untreated tomatoes are dead because of late blight disease. The plants treated with the 400 ppm concentration are healthy with little sign of disease. 2-Cyano-2-methoxyimino-N-(3′-methoxypropyl)carbamoylacetamide can be substituted for 2-cyano-2-methoxyimino-N-methoxymethylcarbamoylacetamide with like results.

EXAMPLE 6

The formulation of Example 5 can be mixed in a spray tank with the fungicide benomyl. The formulation can be diluted to a concentration of 500 ppm of the active ingredient. The benomyl in the mixture should be at a concentration of 100 ppm. Spray can be applied to the point of run-off each week during the growing season to a cucumber field subject to infection by the downy mildew fungus (*Pseudoperonospora cubensis*), the powdery mildew fungus (*Erysiphe chichoracearum*), and the gummy stem blight fungus (*Mycosphaerella citrullina*), The plants which are sprayed with this mixture will be healthy and bear normal crop whereas the unsprayed plants will be damaged by one or more of the fungi listed.

EXAMPLE 7

Potted greenhouse-grown tomato plants are inoculated by spraying them with a spore suspension of *P. infestans*. They are incubated in a saturated humidity chamber at 20°C. for 8 hours. The infected tomato plants are removed from the incubation chamber long enough to spray them with various disease-control agents and combinations of these agents. The formulation of Example 5 is dispersed at a concentration of 400 ppm of the active ingredient. Similar dispersions are made of the commercial fungicides, maneb, captafol, metiram, and chlorthalonil. Additional treatments are made by mixing each of these dispersions of commercial fungicides with an equal quantity of the formulation of this example. This results in 200 ppm of each of the two component active ingredients. Six infected plants are sprayed with enough dispersion to have run-off of dry plants. After treatment, the plants are returned to the humidity chamber for a total of 24 hours. After an additional five days incubation in the greenhouse, the untreated plants are dead because of the late blight disease. Those plants treated with only the commercial fungicides are completely defoliated. The plants treated with the formulation of this invention have only a few restricted lesions. Most of the foliage is healthy. This is because of the unique curative action of the compounds of this invention.

EXAMPLE 8

Potted greenhouse-grown tomato plants are inoculated by spraying them with a spore suspension of *P. infestans*. They are incubated in a saturated humidity chamber at 20°C. for 20 hours. The infected tomato plants are removed from the incubation chamber long enough to spray them with various disease control agents. The compounds listed below are dispersed at a concentration of 400 ppm of the active ingredient. Three infected plants are sprayed with enough dispersion to have run-off of dry plants. After treatment, the plants are placed in a greenhouse for an additional five days incubation. The untreated plants are dead because of the late blight disease. The treated plants are rated for percent of foliage which is healthy (percent disease control). The curative action of the compounds of this invention is demonstrated in the following table.

| Compound | Percent Disease Control |
| --- | --- |
| 2-cyano-2-methoxyimino-N-methoxymethylcarbamoylacetamide | 96 |
| 2-cyano-2-methoxyimino-N-(3′ methoxypropyl)-carbamoylacetamide | 99 |
| Water treatment check | 0 |

EXAMPLE 9

A wettable powder formulation can be prepared as follows:

| | Percent |
| --- | --- |
| 2-cyano-2-ethoxyimino-N-(3′-methoxypropyl)-carbamoylacetamide | 80 |
| sodium alkylnaphthalenesulfonate | 2 |
| sodium ligninsulfonate | 2 |
| synthetic amorphous silica | 3 |
| Keolinite | 13 |

The ingredients can be thoroughly blended, passed through a hammer-mill to produce an average particle size under 40 microns, reblended and sifted through a U.S.S. No. 50 sieve (0.3 mm openings) before packaging.

Apply this formulation as follows: Select a potato field in which there is a uniform but light infection of the late blight disease and in which the older foliage of each plant supports one or two sporulating *phytophthora infestans* lesions. The plant damage at this point should be slight, but the potential for disease spread will be high. Designate plots five rows wide and 20 meters long. Assign treatments to various plots randomly through the field leaving much of the field untreated as buffers between treated plots. Select a series of treatments for application immediately following weather conditions conducive to disease spread. Among those treatments should be the formulation of this example dispersed in water at a concentration of 300 ppm of active ingredient. Apply in other treatments a representation of commercially available fungicides such as maneb, captafol, and chlorthalonil, at their recommended use rate. In addition to these single compound applications, apply combinations of the formulation of this example with each of the commercial fungicides at rates one-half of that used alone. Spray applications should be made immediately after an overnight rain which has the potential of spreading the disease. After 1–2 weeks, the untreated foliage in this field will be completely killed by the blight disease. Those plots receiving treatments of commercial fungicides will be severely diseased and more than 80% defoliated. Those plots receiving the formulation of this example will be protected from the late blight disease and only slightly defoliated. Those plots receiving the combination of the formulation of this invention plus a commercial fungicide will be healthy and free of active disease. The other compounds of this invention may be substituted with like results.

EXAMPLE 10

An aqueous suspension can be prepared as follows:

|  | Percent |
|---|---|
| 2-cyano-2-ethoxyimino-N-methoxymethyl-carbamoylacetamide | 25 |
| hydrated attapulgite | 3 |
| crude calcium ligninsulfonate | 10 |
| disodium hydrogen phosphate | 0.5 |
| water | 61.5 |

The ingredients can be ground together in a ball or roller mill until the solid particles have been reduced to diameters under 10 microns.

An established field of broccoli, in which downy mildew (*Peronospora parasitica*) is just appearing, can be selected for treatment. Randomized plots throughout the field can be sprayed with the formulation of this example dispersed in water at a concentration of 400 ppm active ingredient. Other plots can be treated with commercial fungicides such as maneb, zineb, captofol, chlorothalonil and Bordeaux mixture. Spray applications can be made on 7 to 10 day intervals, preferably after a rain or other natural infection period. At harvest time plants in the untreated plots will be more than 50 percent infected and produce little or no yield. Plants sprayed with the commercial fungicides will be about 20 percent infected with serious loss in yield. Plants treated with the formulation of this example will be free of downy mildew and produce a normal yield.

EXAMPLE 11

A wettable powder can be prepared as follows:

|  | Percent |
|---|---|
| 2-cyano-2-methoxyimino-N-methoxymethylcarbamoylacetamide | 80 |
| sodium dioctyl sulfosuccinate | 1 |
| sodium ligninsulfonate | 2 |
| attapulgite | 17 |

The ingredients can be blended and passed through a hammer mill fitted with a coarse screen. After reblending, it is finely ground in a hammer mill and packaged.

Greenhouse-grown grape plants can be inoculated by spraying with a spore suspension of *Plasmopara viticola*, downy midlew. After 20 hours incubation in a 20°C. saturated humidity chamber, six of the plants can be sprayed to run-off with the above formulation dispersed in water to give 100 ppm active ingredient. Treatments with maneb at 2,000 ppm active can be made on similar plants. After two weeks incubation in a greenhouse, the untreated plants and plants treated with maneb will be severely infected with downy mildew (about 90 percent of the susceptible leaves will be infected). Plants treated with the above formulation will be free of disease, demonstrating the curative effect.

EXAMPLE 12

| Wettable Powder | Percent |
|---|---|
| 2-cyano-N-(3'-methoxypropyl)carbamoyl-2-methoxyiminoacetamide | 40 |
| dioctyl sodium sulfosuccinate | 1.5 |
| sodium ligninsulfonate | 3 |
| low viscosity methyl cellulose | 1.5 |
| attapulgite | 54 |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 13

| Wettable Powder | Percent |
|---|---|
| 2-cyano-N-methoxymethylcarbamoyl-2-methoxyiminoacetamide | 80 |
| sodium alkylnaphthalenesulfonate | 2 |
| sodium ligninsulfonate | 2 |
| synthetic amorphous silica | 3 |
| Kaolinite | 13 |

The ingredients are blended and then passed through a hammer mill to produce 95 percent smaller than 44 microns (U.S.S. No. 325 net screen). After sifting through a screen with 0.3 mm openings (U.S.S. No. 50), the product is packaged.

EXAMPLE 14

| Oil Suspension | Percent |
|---|---|
| 2-cyano-N-methoxymethylcarbamoyl-2-methoxyiminoacetamide | 25 |
| polyoxyethylene sorbitol hexaoleate | 5 |
| highly aliphatic hydrocarbon oil | 70 |

The ingredients are ground together in a sand mill until the solid particles have been reduced to under about 5 microns. The resulting thick suspension may be applied directly, but preferably after being extended with oils or emulsified in water.

EXAMPLE 15

| Dust | Percent |
|---|---|
| 2-cyano-N-(3'-methoxypropyl)carbamoyl-2-methoxyiminoacetamide | 10 |
| attapulgite | 10 |
| pyrophyllite | 80 |

The active ingredient is blended with attapulgite and then passed through a hammer mill to produce particles substantially all below 200 microns. The ground concentrate is then blended with powdered pyrophyllite until homogeneous.

I claim:
1. A compound of the formula

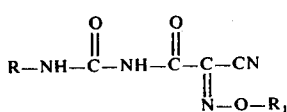

wherein R is $CH_3OCH_2-$ or $CH_3O(CH_2)_3-$ and $R_1$ is alkyl of 1 or 2 carbons.

2. The compound of claim 1 wherein $R_1$ is methyl.

3. A composition useful for inhibiting fungus disease in plants consisting essentially of a fungus inhibiting amount of a compound of claim 1.

4. A composition of claim 3 wherein $R_1$ is methyl.

5. A method of protecting plants from fungus disease consisting essentially of applying to the plants an amount of a compound of claim 1 sufficient to inhibit the fungus disease.